US007732156B2

(12) United States Patent
Heinegard

(10) Patent No.: US 7,732,156 B2
(45) Date of Patent: Jun. 8, 2010

(54) SANDWICH IMMUNOASSAY AND MONOCLONAL ANTIBODIES FOR COMP, CARTILAGE OLIGOMERIC MATRIX PROTEIN

(75) Inventor: Dick Heinegard, Lund (SE)

(73) Assignee: Anamar Medical AB, Uppsala (SE)

( * ) Notice: Subject to any disclaimer, the term of this patent is extended or adjusted under 35 U.S.C. 154(b) by 560 days.

(21) Appl. No.: 11/594,752

(22) Filed: Nov. 9, 2006

(65) Prior Publication Data

US 2007/0154969 A1 Jul. 5, 2007

Related U.S. Application Data

(63) Continuation of application No. 10/130,507, filed as application No. PCT/SE00/02294 on Nov. 22, 2000, now abandoned.

(30) Foreign Application Priority Data

Nov. 22, 1999 (SE) .................................... 9904236

(51) Int. Cl.
*G01N 33/53* (2006.01)
(52) U.S. Cl. .......................... 435/7.9; 435/7.1; 435/7.2; 435/7.91; 435/7.94; 435/344.1; 435/325; 436/514; 436/518; 436/547; 436/548
(58) Field of Classification Search .................. 435/7.1, 435/7.2, 7.91, 7.94, 344.1, 325; 436/514, 436/518, 547, 548
See application file for complete search history.

(56) References Cited

U.S. PATENT DOCUMENTS

| 4,778,768 | A  | 10/1988 | Heinegard et al. |
| 6,849,594 | B1 | 2/2005  | Chen et al. |

FOREIGN PATENT DOCUMENTS

| FR | 2788603    | 7/2000  |
| WO | WO96/01847 | 1/1996  |
| WO | WO98/07035 | 2/1998  |
| WO | WO98/46253 | 10/1998 |

OTHER PUBLICATIONS

V. Vilim et al., "Characterization of Monoclonal Antibodies Recognizing Different Fragments of Cartilage Oligomeric Matrix Protein in Human Body Fluids", Archives of Biochemistry and Biophysics, vol. 341, No. 1, pp. 8-16, (May 1997).
C. Marti et al., "Cartilage Oligomeric Matrix Protein (COMP): The Role of a Non-Collagen Cartilage Matrix Protein As a Marker of Disease Activity and Joint Destruction in Patients With Rheumatoid Arthritis and Osteoarthritis", Abstract of Z. Rheumatol, vol. 58 (2), pp. 79-87, (1999).
M. Neidhart et al., "Small Fragments of Cartilage Oligomeric Matrix Protein in Synovial Fluid and Serum As Markers for Cartilage Degradation", Abstract of Br. J. Rheumatol, vol. 36, pp. 1151-1160, (1997).
Sa Kuhne et al., "Persistent High Serum Levels of Cartilage Oligomeric Matrix Protein in a Subgroup of Patients With Traumatic Knee Injury", Abstract of Rheumatol Int., vol. 18(1), pp. 21-25, (1998).
T. Saxne et al., "Cartilage Oligomeric Matrix Protein: A Novel Marker of Cartilage Turnover Detectable in Synovial Fluid and Blood", British Journal of Rheumatology, vol. 31, pp. 583-591, (1992).
B. Mansson et al., "Cartilage and Bone Metabolism in Rheumatoid Arthritis Differences Between Rapid and Slow Progression of Disease Identified by Serum Markers of Cartilage Metabolism", J. Clin. Invest., vol. 95, pp. 1071-1077, (Mar. 1995).
F.A. Wollheim et al., "HLA DRBI Typing and Cartilage Oligomeric Matrix Protein (COMP) As Predictors of Joint Destruction in Recent-Onset Rheumatoid Arthritis", British Journal of Rheumatology, vol. 36, pp. 847-849, (1997).
I.F. Petersson et al., "Changes in Cartilage and Bone Metabolism Identified by Serum Markers in Early Osteoarthritis of the Knee Joint", British Journal of Rheumatology, vol. 37, pp. 46-50, (1998).
E. Hedbom et al., "Cartilage Matrix Proteins. An Acidic Oligomeric Protein (COMP) Detected Only in Cartilage", J. Biol. Chem., vol. 267, pp. 6132-6136, (Mar. 1992).
Hummel, et al.; Analysis of cartilage oligomeric matrix protein (COMP) in synovial fibroblasts and synovial fluids, Br. J. Rheumatol. vol. 37(7) pp. 721-728 (1998).
Communication Pursuant to Article 115(2) EPC and enclosed Third Party Observations from Rott, Ruzicka & Guttmann, dated Jul. 4, 2005 (EP 00979120.3).
Application for Grant No. NK 4887, Printed 2005.
Internet printout entitled "CEP—detail projektu", containing data and footnotes of project No. NK4887 and English translation, Jan. 1998-Dec. 2000.
Declaration of the Research and Development Council of the Government of the Czech Republic of Jul. 23, 2004 and English translation.

*Primary Examiner*—Bao-Thuy L Nguyen
(74) *Attorney, Agent, or Firm*—Finnegan, Henderson, Farabow, Garrett & Dunner, LLP

(57) ABSTRACT

The present invention provides a new sensitive direct sandwich assay for determining the presence of COMP in a clinical sample. Two monoclonal antibodies directed against separate antigenic determinants of the COMP molecules are used in the assay. The invention also relates to three particularly advantageous monoclonal antibodies per se that are directed against human COMP. Cell cultures manufacturing these antibodies have been deposited according to the Budapest Treaty at Deutsche Sammlung von Mikroorganismen und Zellkulturen GmbH, and have been assigned accession numbers DSM ACC2406, DSM ACC2408 and DSM ACC2418, respectively. A diagnostic kit comprising at least two of these monoclonal antibodies also constitute a part of the present invention.

1 Claim, 1 Drawing Sheet

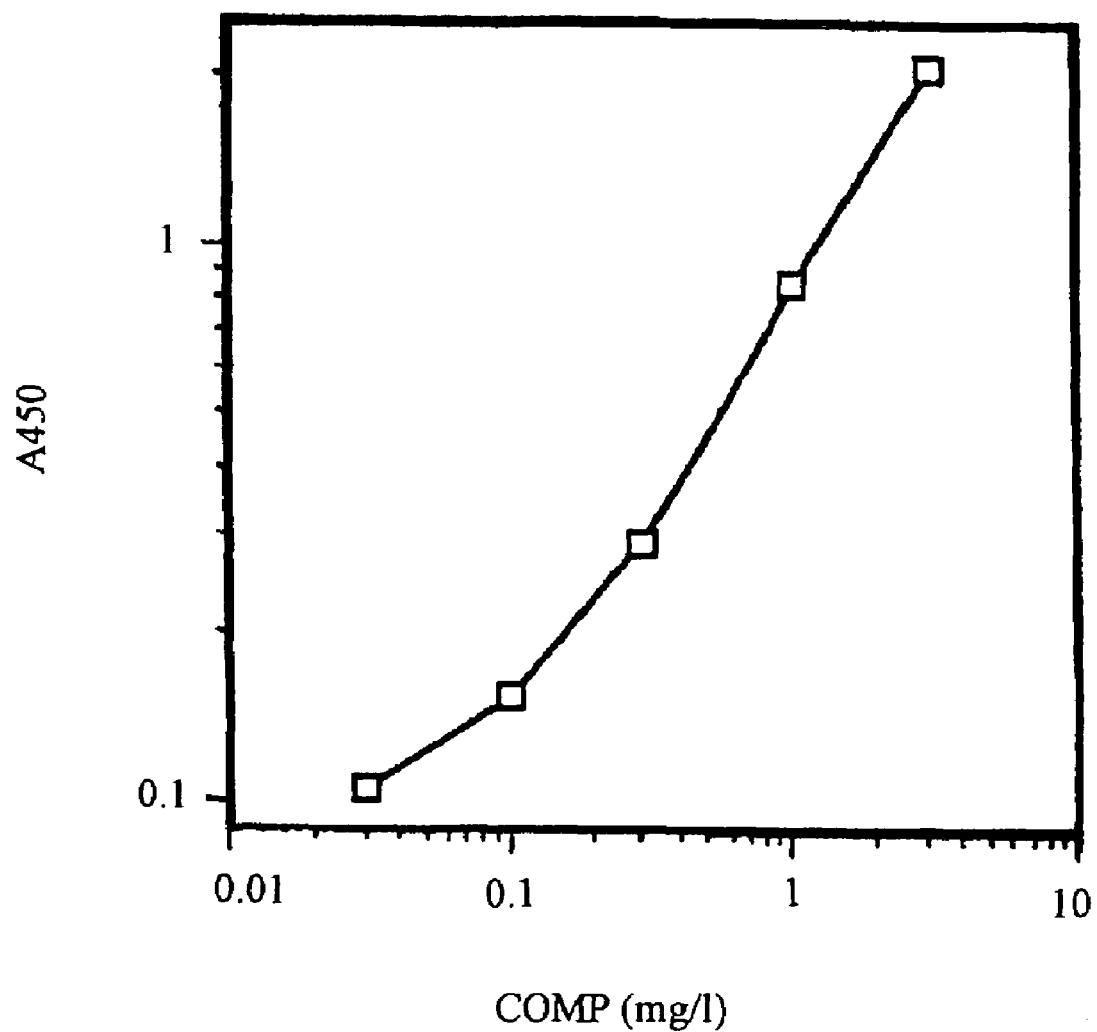

SANDWICH IMMUNOASSAY AND MONOCLONAL ANTIBODIES FOR COMP, CARTILLAGE OLIGOMERIC MATRIX PROTEIN

This is a continuation of U.S. application Ser. No. 10/130,507, filed Sep. 25, 2002, now abandoned which claims the benefit of PCT/SE00/02294, filed on Nov. 22, 2000, in the PCT and 9904236-8, filed Nov. 22, 1999, in Sweden, all of which are incorporated herein by reference.

The present invention relates to a novel sandwich immunoassay for determining the presence of Cartilage Oligomeric Matrix Protein (COMP) in a clinical sample. The invention also relates to two novel monoclonal antibodies directed against COMP as well as cell lines producing these antibodies.

TECHNICAL BACKGROUND

Pathological conditions resulting in cartilage degeneration constitute a major medical, social and economical problem. Of persons older than 65 years of age, 486 per 1,000 have arthritis. Traditionally, the clinical diagnosis of arthritis is based on the patient's history, physical examination, and radiographs. The prognosis, treatment, and clinical outcomes of patients with arthritis are assessed by serial examinations. In order to minimise permanent tissue damage caused by pathological conditions involving cartilage degeneration, it is important to be able diagnose such conditions at an early stage. However, many patients do not develop symptoms until late in the disease process. When a diagnosis is established, permanent tissue damage has often already been formed, and then it is no longer possible for the patient to recover completely.

Accordingly, there is a need for methods for diagnosing pathological cartilage degeneration based upon detection of biologic markers, which markers are released early in the disease progress. Much efforts have been made in finding suitable markers, and parts of this work are reviewed in Lohmander. Ballière's Clinical Rheumatology, vol. 11, p. 711-726; and in Scher et al., the American Journal of Orthopedics, April 1996, p. 263-272.

One possible marker that could be used in such a diagnosis method is COMP, Cartilage Oligomeric Matrix Protein. Elevated serum levels of COMP has previously been associated with joint destruction in rheumatoid arthritis (Månsson et al., J. Clin. Invest. (1995), vol. 95, pp. 1071-1077; Wollheim et al., British Journal of Rheumatology (1997), vol. 36, pp. 847-849; Petersson et al., British Journal of Rheumatology (1998), vol. 37, pp. 46-50). Significant amounts of small fragments of COMP have also been found in synovial fluid from patients with rheumatoid arthritis and other forms of inflammatory arthritis (Neidhardt et al., British Journal of Rheumatology 1997, 36: 1151-60).

It has also been suggested to use COMP or nucleic acid sequences encoding COMP for preparing a pharmaceutical composition for preventing and/or treating arthritic conditions in a mammal (WO 98/46253). Accordingly, COMP can be regarded as a key compound when diagnosing and/or treating different forms of arthritis.

Up till now, COMP has been analysed by an ELISA assay which is based upon polyclonal antibodies (Saxne et al., British Journal of Rheumatology (1992), vol. 31, pp. 583-591). A sample that is suspected to contain human COMP is added to polystyrene microtiter plates. The present COMP is then adsorbed to the plates. Rabbit antihuman COMP antibodies are added and are allowed to bind. Subsequently porcine anti-rabbit antibodies conjugated with alkaline phosphatase are added. A substrate for alkaline phosphatase, para-nitrophenyl phosphate, is finally added and the resulting absorbance at 405 nm can be regarded as a measurement of COMP.

Because of the fact that COMP is such an interesting pathological cartilage degeneration marker is very important to have access to an accurate and sensitive assay rendering it easy to make a distinction between healthy and pathological samples. Accordingly, there is a need for an improved assay method for determining the presence of COMP in a clinical sample.

SUMMARY OF THE INVENTION

The present invention provides a new sensitive direct sandwich assay for determining the presence of COMP in a clinical sample. Two monoclonal antibodies directed against separate antigenic determinants of the COMP molecules are used in the assay. The invention also relates to three particularly advantageous monoclonal antibodies per se that are directed against human COMP. Cell cultures manufacturing these antibodies have been deposited according to the Budapest Treaty at Deutsche Sammlung von Mikroorganismen und Zellkulturen GmbH Maseheroder Weg 1b. D-38124 Braunschweig, on Aug. 25, 1999, and have been assigned accession numbers DSM ACC2406, DSM ACC2408 and DSM ACC2418, respectively. A diagnostic kit comprising at least two of these monoclonal antibodies also constitute a pail of the present invention.

DEFINITIONS

As disclosed herein, the term "clinical sample" relates to a sample originating from a human, and which sample is suspected of containing human COMP. Examples of such samples are blood samples, serum samples, and synovial fluid samples.

As disclosed herein, the term "solid phase carrier" relates to carriers commonly used in immunoassay techniques, such as beads, nanoparticles, magnetic beads and particles, as well as wells of a microtiter plate. In the inventive method, the first monoclonal antibody is either covalently or non-covalently bound to the solid phase using techniques that are frequently utilised in the field.

As disclosed herein, the term "detectable marker" relates to markers and labels commonly used in the field, such as radioactive, enzymatic, and fluorescent labels. Non-radioactive lables are preferably used. Examples of suitable enzymatic labels are alkaline phosphatase and peroxidase. The detection is preferably carried out by incubating the complex to be detected together with substrate giving a colored or fluorescent product that can be monitored spectrophotometrically or fluorometrically.

FIGURES

The present invention is disclosed with reference to the enclosed FIGURE, in which:

FIG. 1 discloses a standard curve for determining the concentration of COMP in a clinical sample. The curve shows the absorbance at 450 nm as a function of the concentration of COMP in mg/l.

DETAILED DESCRIPTION OF THE INVENTION

The present invention relates to a sandwich immunoassay for determining the presence of COMP in a clinical sample, such as blood samples, serum samples, and synovial fluid samples. The clinical sample is first incubated together with a first monoclonal antibody directed against human COMP. This first antibody is bound to a solid phase carrier. According to the invention, the solid phase carrier is a carrier commonly used in immunoassay techniques, such as a bead, nanoparticle, magnetic beads and particles, as well as a well of a microtiter plate. In the inventive method, the first monoclonal antibody is either covalently or non-covalently bound to the solid phase using techniques that are frequently utilised in the field.

After washing away unbound components of the sample using well-known steps, the complex of COMP and the first monoclonal antibody is exposed to a solution containing a second monoclonal antibody against human COMP. It is important that the first and second monoclonal antibodies are not directed against the same antigenic epitope on the human COMP molecule. The second monoclonal antibody is labeled with a detectable marker. A detectable marker with in the context of the present invention is marker or a label commonly used in the field, such as radioactive, enzymatic, and fluorescent labels. Non-radioactive lables are preferably used. Examples of suitable enzymatic labels are alkaline phosphatase and peroxidase. The detection is preferably carried out by incubating the complex to be detected together with substrate giving a coloured or fluorescent product that can be monitored spectrophotometrically or fluorometrically.

After the incubation the reaction is washed in order to remove unbound components. Then the amount of human COMP in the clinical sample is determined using well-known methods which depend upon the particular label that has been used.

It is preferred to use antibodies produced by the cell lines deposited at the Deutsche Sammlung von Mikroorganismen und Zellkulturen GmbH under the accession numbers DSM ACC2406, DSM ACC2408, and DSM ACC2418, respectively, in the present invention.

The present invention will now be described with reference to the enclosed example and preparation. It will be understood by the skilled person that the scope of the present invention is only limited by the claims and not by the examples.

Preparation of COMP:

30 g cartilage of human or rat origin are homogenised at 0° C. in 10 volumes of extraction buffer I (0.15 M NaCl, 0.100 M ε-aminocaproic acid, 0.005 M benzamidine-HCl, 0.005 M Tris, pH 7.4, and 10 mM NEM (N-ethyl maleimide)). The homogenate is then shaken at 4° C. for 1 h. Subsequently, the homogenate is centrifugated at 4° C. and at 20,000×g for 20 minutes. The supernatant is discarded and the pellet is suspended in extraction buffer II (0.15 M NaCl, 0.010 M EDTA, 0.100 M ε-aminocaproic acid, 0.005 M benzamidine-HCl, 0.005 M Tris, pH 7.4, and 10 mM NEM (N-ethyl maleimide)). The suspension is then shaken overnight at 4° C., and then it is centrifugated at 4° C. and at 20,000×g for 20 minutes. The supernatant is diluted with equal amounts of deionised water. A DEAE sepharose column (about 30-40 ml) is equilibrated with at least 3 column volumes of buffer A (0.005 M Tris-HCl, pH 7.4, 0.001 M EDTA, 0.075 M NaCl). The diluted supernatant is then applied to the column overnight, and the column is washed with at least 3 column volumes of buffer A. A gradient from buffer A to buffer B (0.005 M Tris-HCl, pH 7.4, 0.001 M EDTA, 0.500 M NaCl)(2×250 ml) is run and fractions are collected.

COMP can also be obtained from chondrosarcoma cell lines by affinity chromatography using immobilised antibodies against COMP. The chromatography is carried out using common techniques such as washing with a neutral buffer and eluation with high salt concentration or a low pH.

It turns out that rat COMP and human COMP are almost immunologically equivalent (data not shown) and that rat COMP can be used as internal standard when carrying out the present assay method.

Example

Blood samples are collected by venipuncture and are allowed to clot. Serum is separated by centrifugation. Alternatively, blood is collected by venipuncture into tubes containing heparin or EDTA as coagulant and the plasma fraction is separated. The samples are the diluted 1:20 in sample diluent (0.05 M Tris-HCl, pH 7.5, 0.90% (wt) NaCl, 1% bovine serum albumine, 0.05% Tween 20, 0.15% Cathone CG, 0.01% tartazine, 0.001 M $CaCl_2$, 0.01% bovine IgG, sterile-filtered using a 0.45 μm filter) (25 μl sample to 500 μl sample diluent).

Each determination is performed in duplicate for standards an unknown samples. A standard curve is prepared for each assay run. FIG. 1 shows an example of a standard curve obtained according to the present method. A polystyrene 96 wells microtiter plate, wherein the monoclonal antibody produced by cell line DSM ACC2406 are immobilised in the wells, is used. In order to prepare a standard curve 25 μl of solutions containing 0.03, 0.1, 0.3, 1 and 3 mg/l COMP were added to some wells. 25 μl of unknown sample are added to the others. 100 μl conjugate solution diluent containing the monoclonal antibody produced by the cell line DSM ACC2408 conjugated to horseradish peroxidase (0.05 M Tris-HCl, pH 7.5, 0.90% (wt) NaCl, 1% bovine serum albumine, 0.05% Tween 20, 0.15% Cathone CG, 0.03% patent blue, 0.001 M $CaCl_2$, 0.01% bovine IgG, 0.005% heterophilic blocking reagent-1, sterile-filtered using a 0.45 μm filter) are added to all wells and the plate are incubated on a shaker for 90 minutes at room temperature. The plate is washed 6 times with phosphate-buffered saline, pH 7.4. 200 μl 3,3',5,5'-tetramethylbenzidine (1 mM) are added to each well and the plate is incubated for 15 minutes at room temperature. The colour reaction is stopped by adding 50 μl 1 M $H_2SO_4$ to each well. The absorbance at 450 nm is measured, a standard curve is prepared and the unknown samples are evaluated.

The invention claimed is:

1. A method of analysing the presence of human COMP (cartilage oligomeric matrix protein) in a clinical sample, comprising a) providing a first monoclonal antibody directed against human COMP, which first monoclonal antibody is bound to a solid phase carrier;

b) adding a clinical sample suspected to contain human COMP together with the first monoclonal antibody of step a) and incubating the resulting mixture in aqueous solution;

c) adding a second monoclonal antibody directed against human COMP to the mixture of step b), said second monoclonal antibody comprising a label emitting a detectable and quantifiable signal, where said second monoclonal antibody is not directed against the same COMP epitope as said first monoclonal antibody; and d) quantifying the signal from the label, said signal being a measurement of the concentration of human COMP in said sample, wherein said first monoclonal antibody and said second monoclonal antibody are different and are chosen from the monoclonal antibodies produced by cell lines deposited at the Deutsche Sammlung von Mikrorpanismen und Zellkulturen GmbH under the accession numbers DSM ACC2406, DSM ACC2408, and DSM ACC2418, respectively.

* * * * *

UNITED STATES PATENT AND TRADEMARK OFFICE
CERTIFICATE OF CORRECTION

| | | |
|---|---|---|
| PATENT NO. | : 7,732,156 B2 | Page 1 of 1 |
| APPLICATION NO. | : 11/594752 | |
| DATED | : June 8, 2010 | |
| INVENTOR(S) | : Dick Heinegard | |

It is certified that error appears in the above-identified patent and that said Letters Patent is hereby corrected as shown below:

Title page, item (30), under Foreign Application Priority Data,

"Nov. 22, 1999   (SE) ...................... 9904236"
should read
-- Nov. 22, 1999   (SE) ...................... 9904236-8 --.

Signed and Sealed this

Seventh Day of September, 2010

David J. Kappos
*Director of the United States Patent and Trademark Office*